United States Patent
Zimmermann et al.

(12)

(10) Patent No.: US 6,222,063 B1
(45) Date of Patent: Apr. 24, 2001

(54) PROCESS FOR TRANSESTERIFYING α-KETOCARBOXYLIC ESTERS

(75) Inventors: Curt Zimmermann, Mauthausen; Johann Friedhuber, Linz, both of (AT)

(73) Assignee: DSM Fine Chemicals Austria GmbH, Linz (AT)

( * ) Notice: Subject to any disclaimer, the term of this patent is extended or adjusted under 35 U.S.C. 154(b) by 0 days.

(21) Appl. No.: 09/369,384

(22) Filed: Aug. 6, 1999

(30) Foreign Application Priority Data

Aug. 7, 1998 (AT) .................................................. 1365/98

(51) Int. Cl.$^7$ .................................................. C07C 69/66
(52) U.S. Cl. ................. 560/174; 51/53; 51/234; 556/54; 556/56
(58) Field of Search ........................ 556/54, 56; 560/53, 560/121, 122, 123, 124, 174, 217, 234, 51

(56) References Cited

U.S. PATENT DOCUMENTS 3,121,109    2/1964   Young .
4,112,235  * 9/1978   Schmerling et al. .
5,614,650    3/1997   Sandler et al. .

OTHER PUBLICATIONS

Masumizu et al. Tetrahedron Lett. vol. 27, No. 1, (1986) pp. 55–56.*

* cited by examiner

*Primary Examiner*—Gary Geist
*Assistant Examiner*—Robert W. Deemie
(74) *Attorney, Agent, or Firm*—Wenderoth, Lind & Ponack, L.L.P.

(57) ABSTRACT

Process for transesterifying α-ketocarboxylic esters in an anhydrous alcohol as reaction medium in the presence of tin catalysts, titanium catalysts, zirconium catalysts or lithium catalysts or of acetylacetonates as catalysts.

10 Claims, No Drawings

PROCESS FOR TRANSESTERIFYING α-KETOCARBOXYLIC ESTERS

α-Ketocarboxylic esters, such as ethyl pyruvate (PAEE), are used in a multiplicity of areas, for instance as intermediates for agricultural and pharmaceutical active compounds, as solvents etc. However, preparation processes employed hitherto have proved unsuitable from the economic and technical aspect for the most varied reasons. Thus, for example, preparing PAEE similarly to methyl pyruvate (PAME) by ozonolysis and subsequent reduction starting from ethyl methacrylate in ethanol instead of methyl methacrylate in methanol has considerable disadvantages. Firstly, ethyl methacrylate is considerably more expensive than methyl methacrylate, secondly, the by-product formaldehyde is not completely acetalated with ethanol as solvent, as a result of which an interfering residual content of formaldehyde remains for the further work-up, thirdly, because of the heavier formaldehyde diethylacetal formed, during the work-up more by-product must be burned and, fourthly, the ketal cleavage in the case of PAEE diethylketal proceeds with much more difficulty than with PAME dimethylketal.

According to J. Liebigs Ann. Chem., 564, 34 (1949), PAEE is prepared in only 53% yield by esterifying pyruvic acid with absolute ethanol and benzene and subsequently drying the ternary azeotrope ethanol/benzene/water over $K_2CO_3$.

Possibilities have already been investigated of preparing PAEE by transesterifying PAME.

This preparation path, however, has failed to date on the versatile reactivity of the molecule owing to the α-ketocarboxylic acid structural element. Thus, during the transesterification in a basic medium, because of a rapid condensation of the carbonyl group with the adjacent activated methyl or methylene group, unwanted by-products occur, while in an acidic medium, ketals and water are formed, the water in turn leading to unwanted hydrolysis of the ester. Under approximately neutral conditions, acceptable conversion rates are not achieved.

Unexpectedly, it has now been found that, by using special metal catalysts and anhydrous conditions in the reaction medium, transesterification of α-ketocarboxylic esters is possible in good yield and without side reactions.

The present invention therefore relates to a process for transesterifying α-ketocarboxylic esters using an alcohol, which comprises carrying out the transesterification in an anhydrous alcohol as reaction medium in the presence of tin catalysts, titanium catalysts, zirconium catalysts or lithium catalysts or of acetylacetonates as catalysts.

According to the invention, all α-ketocarboxylic esters having the structural element of the formula I

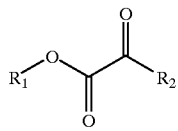

can be transesterified.

$R_1$ and $R_2$ here are a saturated or unsaturated, branched, unbranched or cyclic $C_1$–$C_{30}$ alkyl radical or an aromatic or heteroaromatic radical, where these radicals can have substituents such as $C_1$–$C_{10}$ alkoxy, substituted amino, carbonyl, derivatized carboxyl and underivatized carboxyl, ester, halogen, hydroxyl, nitro substituents, and other nitrogen functions, boron compounds, phosphorus compounds, sulfur compounds or silicon compounds, it being necessary to take care that non-neutrally-reacting functional groups are substantially neutralized either intramolecularly or by acidic or basic additions or solvents, in order to prevent condensation reactions or acid-catalyzed ketalization. Preferably, $R_1$ and $R_2$ are a $C_1$–$C_4$ alkyl radical such as methyl, ethyl, propyl or isopropyl or a benzyl radical. Particular preference is given to the methyl radical.

The process according to the invention is preferably used for transesterifying methyl pyruvate (PAME). The preferred transesterification product is ethyl pyruvate (PAEE).

Transesterification is performed in an anhydrous reaction medium. The reaction medium which is used here is an alcohol $R_3$—OH, where $R_3$ is the radical which is exchanged for $R_1$. $R_3$ is therefore defined as $R_1$ and $R_2$, where $R_1$ and $R_3$ are not identical. Preferably, $R_3$ is therefore a branched or unbranched $C_2$–$C_6$ alkyl radical or a benzyl radical. Preferably, therefore, PAME is reacted in anhydrous ethanol to form PAEE by the process according to the invention.

In addition to the alcohol used, a further anhydrous solvent, such as unsubstituted and substituted alkanes, such as hexane, heptane, etc., alkenes, alkynes, alcohols, substituted amines, amides, aromatics, esters, ethers, halogen compounds, heteroaromatics, lactones, ketones, other nitrogen-containing compounds, such as nitroalkanes, silicon compounds, such as silicone oils, sulfur compounds, such as sulfoxides, can be used, it again being necessary to take care that non-neutrally-reacting functional groups are substantially neutralized either intramolecularly or by acidic or basic additions respectively to the alcohol component or ester component, in order to prevent condensation reactions or acid-catalyzed ketalization.

The transesterification takes place according to the invention in the presence of special metal catalysts. Suitable catalysts are selected from the group consisting of the tin catalysts dialkyltin dicarboxylates, such as dibutyltin dicarboxylates, in particular dibutyltin diacetate, dibutyltin dilaurate, dibutyltin diisooctoate, dibutyltin maleate and mixed dibutyltin dicarboxylates, in particular with relatively long-chain fatty esters, dioctyltin dicarboxylates, in particular dioctyltin dilaurate, trialkyltin alkoxides, such as tributyltin oxide, monoalkyltin compounds, such as monobutyltin dihydroxychloride and monobutyltin dioxide, tin salts such as tin acetate, tin oxalate and tin chloride, tin oxides, such as SnO, selected from the group consisting of titanium catalysts, monomeric and polymeric titanates and titanium chelates such as tetraisopropylorthotitanate, tetrapropylorthotitanate, tetraethylorthotitanate, tetrabutylorthotitanate, tetraisobutylorthotitanate, 2-ethylhexyltitanate, stearyltitanate, cresyltitanate, titaniumacetylacetonate, triethanolaminetitanate, octylene glycol titanate, isostearyltitanate, diethyl citrate titanate selected from the group consisting of the zirconium catalysts, zirconates and zirconium chelates such as tetrapropylzirconate, tetraisopropylzirconate, tetrabutylzirconate, triethanolaminezirconate, diethyl-citrate zirconate, zirconium(IV) acetylacetonate, and lithium catalysts such as lithium salts, lithium alkoxides, and aluminum (III) acetylacetonate, chromium(III) acetylacetonate, iron (III) acetylacetonate, cobalt(II) acetylacetonate, nickel(II) acetylacetonate and zinc(II) acetylacetonate.

Preference is given to dibutyltin diacetate, mixed dibutyltin dicarboxylates with relatively long-chain fatty esters, dioctyltin dilaurate, monobutyltin dihydroxychloride, monobutyltin dioxide, tin acetate, tin oxalate, tin chloride, tetraisopropylorthotitanate, tetrapropylorthotitanate, tetraethylorthotitanate, tetrabutylorthotitanate, tetrapropylzirconate, and also lithium salts and alkoxides and abovementioned acetylacetonates. Particular preference is given to dibutyltin diacetate, tetraisopropylorthotitanate, tetraethylorthotitanate.

The amount of catalyst used is from 0.0001 to 20% by weight, preferably from 0.005 to 5% by weight, and particularly preferably from 0.02 to 1% by weight. The reaction mixture is preferably heated to the boiling point of the reaction mixture, so that the reaction temperature is between 20° C. and 200° C., depending on the reactants. The transesterification can in addition be carried out at atmospheric pressure, but also at reduced pressure or overpressure from 0.001 to 200 bar. The alcohol eliminated in the transesterification is preferably continuously distilled off. Preferably, the reaction is carried out using a distillation tower having a high separation efficiency.

The catalyst, after transesterification is complete, is separated off in good yield by washing with water, hydrolyzing the catalyst and filtering the precipitated metal oxide, or preferably by distilling off the product from the catalyst, preferably on a thin-film or short-path evaporator.

By means of the process according to the invention, conversion rates up to over 99% are achieved, and the yields, without recycling unreacted starting product, are up to over 96%. By recycling the unreacted starting material, yields of up to over 97% may be achieved. Owing to the gentle transesterification conditions, product purities of up to over 99.9% are obtained.

EXAMPLE 1

Transesterification of PAME to PAEE using dibutyltin diacetate without recycling of PAME 800 g (7.8 mol) of methyl pyruvate (99.8% by GC) and 900 g of ethanol (anhydrous) were heated to boiling in a distillation apparatus having a 25-tray bubble-cap tray tower and reflux divider. The distillate at the top of the tower was tested at 100% reflux to be anhydrous (<0.1% water by Karl Fischer). 0.31 g of dibutyltin diacetate was then added in the form of a 10% solution in ethanol. Collection was carried out for a further 2 hours at the tower top at 100% reflux methanol which is formed by the transesterification reaction and distillation was then performed at a ratio of reflux to take-off of 20:1. The filling level in the reaction vessel was kept constant by adding ethanol to the distillation bottom phase. After 12 hours the reaction was virtually complete. This was readily recognizable from the decrease in the amount of methanol collecting at the top of the distillation tower. Excess ethanol was then distilled off at reduced pressure, the bottom temperature not increasing above approximately 90° C. The remaining reaction solution was freed from tin catalyst (30 g of tin-containing distillation bottom phase) on a thin-film evaporator under a reduced pressure of 80 mbar. By fractional distillation at 50 mbar, 880 g (7.6 mol) of ethyl pyruvate having a purity of 99.8% (GC) were obtained. The yield is 96.7%.

In a comparative experiment using ethanol which had a water content of 0.6% (KF), after 12 hours of reaction time, in addition to the desired product, the dimethyl, diethyl and mixed ethyl methyl ketals of the methyl pyruvate and ethyl pyruvate were found by GC-MS analysis. During the workup, 155 g of no longer utilizable thin-film distillation bottom phase were produced. After fractional distillation, 755 g (6.3 mol) of ethyl pyruvate having a purity of 97.1% (GC) were obtained. The yield is 81%.

EXAMPLE 2

Transesterification of PAME to PAEE using dibutyltin diacetate with recycling of PAME.

1000 g (9.8 mol) of methyl pyruvate, 1100 g of ethanol and 0.39 g of dibutyltin diacetate were reacted as in Example 1. After 8 hours, the reaction was terminated. The reaction mixture was worked up as in Example 1. There remained 25 g of tin-containing distillation bottom phase. By fractional distillation, 201 g (2 mol) of unreacted methyl pyruvate having a purity of 98% (GC), which served as starting material for the next experiment, and 884 g (7.6 mol) of ethyl pyruvate having a purity of 99.9% (GC) were obtained. The yield of ethyl pyruvate, based on methyl pyruvate reacted, is 97.3%.

EXAMPLE 3

Continuous transesterification of PAME to PAEE using titanium (IV) isopropanolate 1000 g (9.8 mol) of methyl pyruvate and 20 g of titanium (IV) isopropanolate were dissolved in 750 g of ethanol. In the bottom of a distillation apparatus, consisting of tower, condenser having reflux divider, vessels for reactants and products and pumps for charging and discharging the product streams and for evacuating the apparatus, 300 ml of ethanol were heated under a low vacuum (395 mbar). The starting materials were then charged into the upper third of the tower at a constant rate over a period of 5 hours. During this time, a further 790 g of ethanol were continuously introduced into the bottom of the tower, the bottom temperature being kept at 66° C. The filling level in the bottom vessel was kept at approximately 300 ml by continuous discharge of the reaction mixture. At the top of the tower, the resultant methanol was distilled off at a reflux to take-off ratio of 1:1. After the introduction of the starting materials was ended, all of the reaction mixture produced at the bottom of the tower was combined and worked up as described in Example 2. There remained 80 g of titanium-containing thin-film distillation bottom phase. Fractional distillation gave 158 g (1.55 mol) of unreacted methyl pyruvate and 899 g (7.7 mol) of methyl pyruvate having a purity of 99.7% (GC). The yield of ethyl pyruvate, based on methyl pyruvate reacted, is 94%.

What is claimed is:

1. A process for transesterifying α-ketocarboxylic esters using an alcohol, which comprises carrying out the transesterification in an anhydrous alcohol as reaction medium in the presence of tin catalysts, titanium catalysts, zirconium catalysts or lithium catalysts or of acetylacetonates as catalysts.

2. The process as claimed in claim 1, wherein α-ketocarboxylic esters having a structural element of the formula I

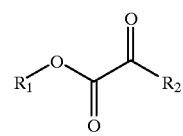

are transesterified with an alcohol of the formula R$_3$OH, where R$_1$, R$_2$ and R$_3$ are a branched, unbranched or cyclic, saturated or unsaturated C$_1$–C$_{30}$ alkyl, aryl or heteroaryl radical, and R$_1$ and R$_3$ are not identical.

3. The process as claimed in claim 1, wherein ketocarboxylic esters of the formula I where R$_1$ and R$_2$ are a branched or unbranched C$_1$–C$_4$ alkyl radical or a benzyl radical are transesterified with an alcohol R$_3$OH, where R$_3$ is not identical to R$_1$ and is a branched or unbranched C$_2$ to C$_6$ alkyl radical or a benzyl radical.

4. The process as claimed in claim 1, wherein methyl pyruvate is transesterified in anhydrous ethanol to form ethyl pyruvate.

5. The process as claimed in claim 1, wherein the catalyst is used in an amount from 0.0001 to 20% by weight, preferably from 0.005 to 5% by weight, and particularly preferably from 0.02 to 1% by weight.

6. The process as claimed in claim 1, wherein the catalyst used is selected from the group consisting of the tin catalysts dibutyltin diacetate, dibutyltin dilaurate, dibutyltin diisooctoate or dibutyltin maleate, mixed dibutyltin dicarboxylates with relatively long-chain fatty esters, dioctyltin dilaurate, monobutyltin dihydroxychloride, monobutyltin dioxide, tin acetate, tin oxalate or tin chloride.

7. The process as claimed in claim 1, wherein the catalyst used is selected from the group consisting of the titanium catalysts tetraisopropylorthotitanate, tetrapropylorthotitanate, tetraethylorthotitanate or tetrabutylorthotitanate.

8. The process as claimed in claim 1, wherein the catalyst used is selected from the group consisting of the zirconium catalysts tetrapropylzirconate.

9. The process as claimed in claim 1, wherein, as acetylacetonate, aluminum (III) acetylacetonate, chromium (III) acetylacetonate, iron(III) acetylacetonate, cobalt(III) acetylacetonate, nickel(II) acetylacetonate or zinc(II) acetylacetonate is used as catalyst.

10. The process as claimed in claim 1, wherein the transesterification is carried out in the presence of an additional solvent.

* * * * *